United States Patent [19]
Kumagai et al.

[11] Patent Number: 5,703,687
[45] Date of Patent: Dec. 30, 1997

[54] METHOD AND APPARATUS FOR INSPECTING THE OUTER APPEARANCE OF A SPHERICAL ARTICLE

[75] Inventors: Hiroki Kumagai; Fumio Fukazawa, both of Chichibu, Japan

[73] Assignee: Bridgestone Sports Co., Ltd., Tokyo, Japan

[21] Appl. No.: 703,695

[22] Filed: Aug. 27, 1996

[30] Foreign Application Priority Data

Aug. 28, 1995 [JP] Japan .................................. 7-242483

[51] Int. Cl.⁶ ................................................ G01N 21/88
[52] U.S. Cl. ................................................ 356/426
[58] Field of Search .................................... 356/426

[56] References Cited

U.S. PATENT DOCUMENTS 4,398,825  8/1983  Lewis ............................. 356/426
5,602,646  2/1997  Bernardin et al. ............... 356/426

*Primary Examiner*—Vincent P. McGraw
*Attorney, Agent, or Firm*—Sughrue, Mion, Zinn, Macpeak & Seas, PLLC

[57] ABSTRACT

An undesirable protrusion on a golf ball is automatically detected by means of an optical system. Light (5) is illuminated to a selected position (3) on the spherical surface of a golf ball (1a) in a tangential direction. The ball (1a) is rotated in line with the light illuminating direction. A line sensor camera (6) is operated to take a line image of the spherical surface in the vicinity of the selected position and along a line perpendicular to the light illuminating direction. A two-dimensional image is constructed from image data of the camera. An abnormal brightness change which appears in the two-dimensional image as a result of an undesirable protrusion (9a, 9b) on the spherical surface shutting out the light (5) is detected, thereby detecting the presence of the undesirable protrusion.

14 Claims, 5 Drawing Sheets

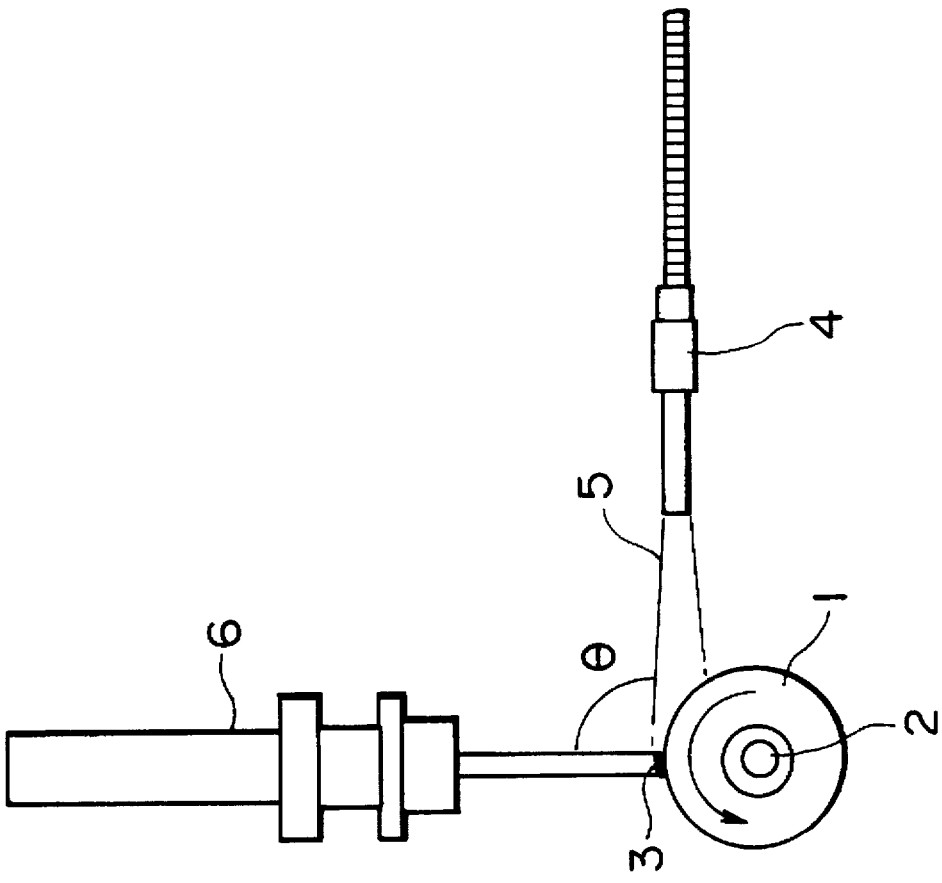
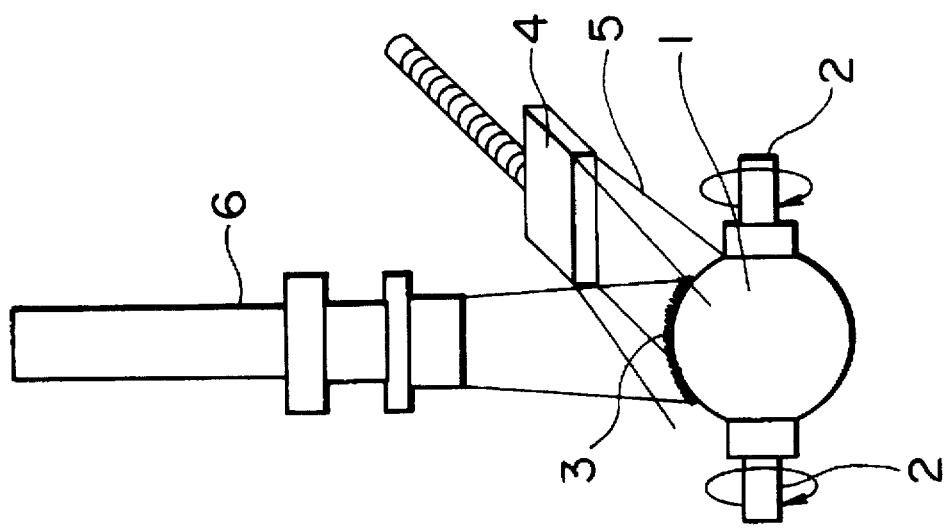

FIG.2
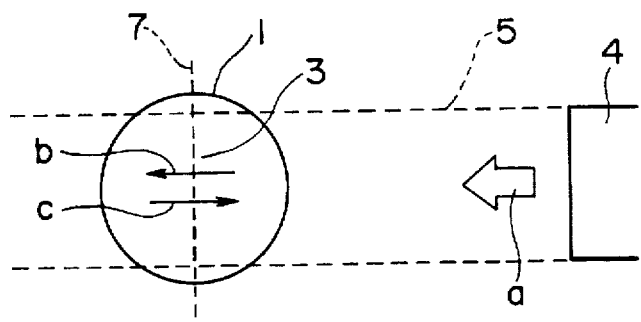
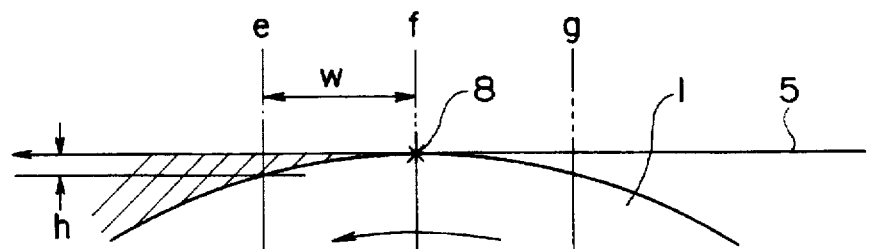
FIG.3A
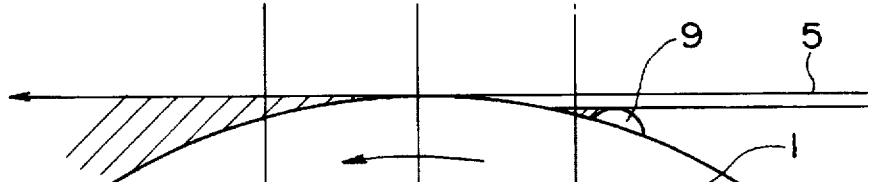
FIG.3B
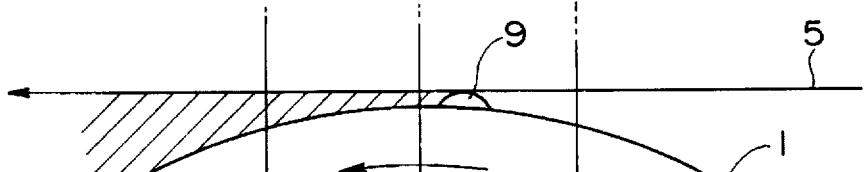
FIG.3C
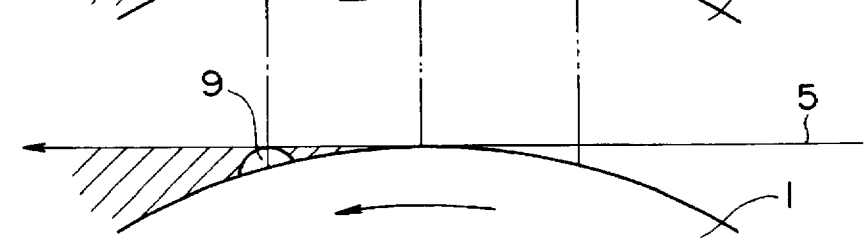
FIG.3D

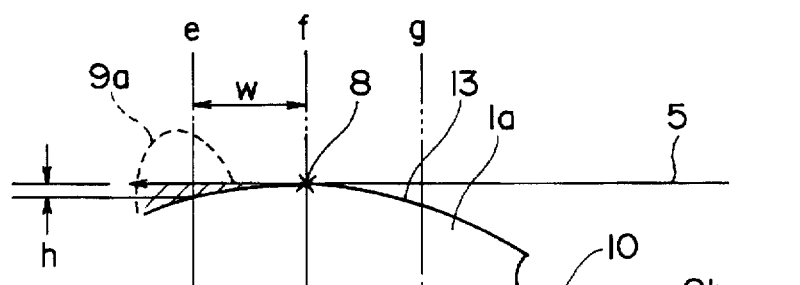
FIG.4 A
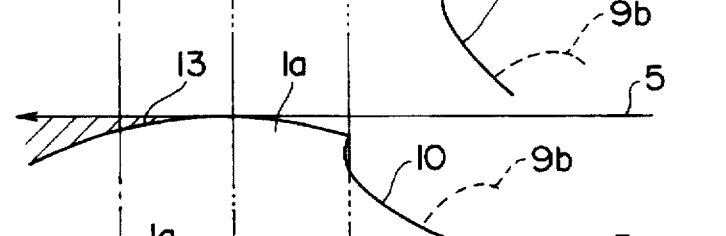
FIG.4 B
FIG.4 C
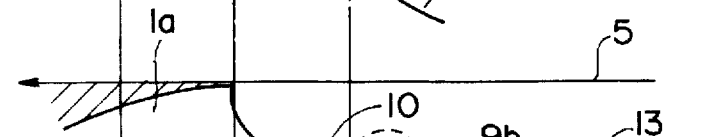
FIG.4 D
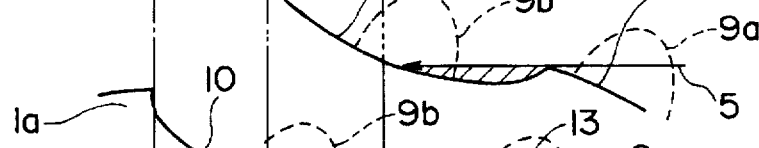
FIG.4 E
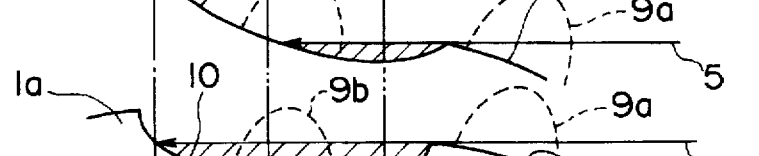
FIG.4 F
FIG.4 G
FIG.4 H
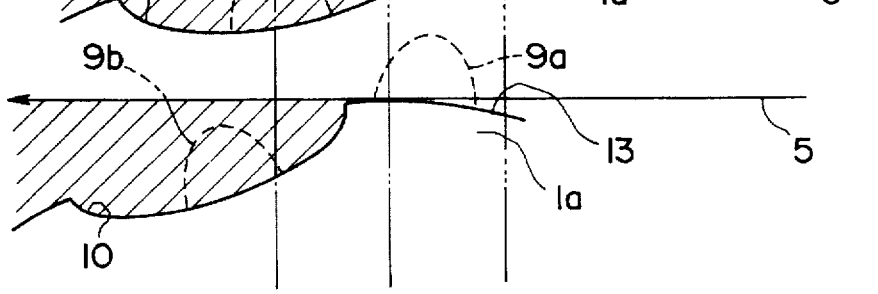

14

METHOD AND APPARATUS FOR INSPECTING THE OUTER APPEARANCE OF A SPHERICAL ARTICLE

BACKGROUND OF THE INVENTION

1. Field of the Invention

This invention relates to a method and apparatus for inspecting the outer appearance of a spherical article for detecting an undesirable protrusion on the surface. More particularly, it relates to a method and apparatus for inspecting the outer appearance of golf balls.

2. Prior Art

In the manufacture of golf balls, undesirable protrusions such as small bumps can be formed on the surface of golf balls. Such undesirable protrusions, even if they are small, can alter the design of dimples formed in the ball surface, affecting the aerodynamics of the ball. It is then a common practice to carry out an outer appearance inspection on golf balls for identifying those balls with undesirable protrusions before shipping.

It has long been desired to incorporate an inspection apparatus in the manufacturing line to automate an outer appearance inspection for detecting undesirable protrusions. Automatic outer appearance inspection is difficult with golf balls because of their special surface topography. The present status of outer appearance inspection is visual observation by workers.

As a substitute for visual inspection, it is commonly employed to automatically inspect the outer appearance of various articles by taking an optical image of an object to be inspected by optical imager means such as a camera, and judging from the image whether or not the outer appearance is acceptable by image processing means. Where the object to be inspected is a spherical article, it is difficult to provide an image which allows for definite discrimination from a normal spherical surface an undesirable protrusion which is a very small bump. Especially in the case of golf balls, their surface is not uniform due to the presence of a plurality of dimples. In other words, the golf ball is a spherical body having a lustrous surface of specific and complex topography. When light is illuminated to the golf ball, there occurs a multiplicity of optical disturbances. It is then very difficult to produce an image having a definite difference between dimples of concave shape and undesirable protrusions of low-profile convex shape.

For this reason, the state-of-the-art outer appearance inspection of golf balls relies on visual observation by workers as mentioned above. The inspection by visual observation imposes a heavy burden to workers. To visually find an undesirable protrusion in the form of a very small bump on a golf ball having a plurality of dimples in its surface is a very difficult operation. On inspecting golf balls by visual observation, workers frequently overlook undesirable protrusions in the form of very small bumps.

SUMMARY OF THE INVENTION

An object of the present invention is to provide a method and apparatus for inspecting the outer appearance of a spherical article, which can detect any undesirable protrusion in the form of a very small bump on a spherical surface, especially on a spherical surface having a plurality of recesses and which can automate the detection operation. Another object of the present invention is to provide a method and apparatus for inspecting the outer appearance of a golf ball for detecting any undesirable protrusion on its spherical surface despite the presence of dimples.

According to a first aspect of the invention, there is provided a method for inspecting the outer appearance of a spherical article, comprising the steps of: illuminating light to a selected position on the spherical surface of the spherical article in a tangential direction; rotating the spherical article in line with the light illuminating direction; operating a line sensor camera to take a line image of the spherical surface in the vicinity of the selected position and along a line perpendicular to the light illuminating direction, the line sensor camera delivering image data; constructing a two-dimensional image from the image data; and detecting an abnormal brightness change which appears in the two-dimensional image as a result of an undesirable protrusion on the spherical surface shutting out the light, thereby detecting the presence of the undesirable protrusion.

According to a second aspect of the invention, there is provided an apparatus for inspecting the outer appearance of a spherical article, comprising rotating means for supporting and rotating the spherical article in a predetermined direction at a predetermined speed; means for illuminating light to a selected position on the spherical surface of the spherical article in a tangential direction and in line with the rotational direction of the spherical article; a line sensor camera for taking a line image of the spherical surface in the vicinity of the selected position and along a line perpendicular to the light illuminating direction; and image converter means for receiving image data from the line sensor camera and constructing a two-dimensional image from the image data. In operation, light is illuminated from the light source to the surface of the spherical article which is being rotated by the rotating means, the surface of the rotating spherical article is photographed by the line sensor camera, a two-dimensional image is constructed from the image data of the line sensor camera by the image converter means, and an abnormal brightness change which appears in the two-dimensional image as a result of an undesirable protrusion on the spherical surface shutting out the light is detected, thereby detecting the presence of the undesirable protrusion.

BENEFITS OF THE INVENTION

In the method and apparatus for inspecting the outer appearance of a spherical article according to the present invention, light is illuminated to a selected position on the spherical surface of the spherical article in a tangential direction, the spherical article is rotated in line with the light illuminating direction, a line sensor camera is operated to take a line image of the spherical surface in the vicinity of the selected position and along a line perpendicular to the light illuminating direction, thereby obtaining image data, a two-dimensional image is constructed from the image data, and an undesirable protrusion on the spherical surface is detected from the two-dimensional image. Where an undesirable protrusion is present on the spherical surface, the undesirable protrusion shuts out light at the selected position and a position shifted backward of the selected position toward the illuminating output, so that an area (forward of the protrusion) that should normally be illuminated with light is kept in the shadow of the protrusion. Inversely, at a position shifted forward of the selected position away from the illuminating output, the undesirable protrusion is illuminated with light as if an area that should normally be in the shadow were illuminated with light. In this way, a change of bright and dark areas appearing in the two-dimensional image is different from the normal change. The presence of an undesirable protrusion is detected from this abnormal change of bright and dark areas, identifying a defective spherical article.

The outer appearance inspecting method and apparatus of the invention utilizes the fact that an article to be inspected is a spherical body such that when light is illuminated to the selected position on the spherical surface in a tangential direction, an abnormal change of bright and dark zones occurs at the selected position as a result of an undesirable protrusion on the spherical surface shutting out the light or being illuminated with the light, and this abnormal change is detected by the line sensor camera taking a picture along the straight line extending at the selected position perpendicular to the illuminating direction of light. The invention makes it possible to detect an undesirable protrusion in the form of a small bump on the spherical surface which is difficult to detect by the prior art technique. Since the illuminating direction of light is a tangential direction at the shooting position, the shooting direction of the line sensor camera can be offset 45 to 90 degrees from the illuminating direction of light. Even when the spherical surface is lustrous, this angular shooting eliminates the inconvenience that light reflected by the spherical surface enters directly the line sensor camera to produce a picture consisting of obscure bright and dark zones, ensuring that an abnormal brightness change due to the presence of undesirable protrusions appears in the picture.

Even if the spherical article to be inspected is a golf ball having a plurality of dimples in the surface, the outer appearance inspecting method of the invention can discriminate undesirable protrusions from the normal spherical surface, ensuring automatic high precision outer appearance inspection. When outer appearance inspection is carried out on a golf ball having a plurality of dimples in the surface according to the present invention, there is obtained a two-dimensional image in which a plurality of bright or dark spots corresponding to the plurality of dimples appear in a dotted pattern. If undesirable protrusions are present on the golf ball surface, the protrusions shut out the illuminating light or are illuminated with the illuminating light independent of whether the protrusions are inside or outside the dimples, necessarily bringing on anomaly in the brightness change of a two-dimensional image, whereby the presence of undesirable protrusions can be acknowledged.

The method and apparatus for inspecting the outer appearance of a spherical article according to the invention makes it possible to detect any undesirable protrusion in the form of a small bump on the spherical surface and to automate the detection process. Since even small undesirable protrusions on the spherical surface having a plurality of recesses or dimples can be detected, the inventive method and apparatus can be advantageously used in inspecting the outer appearance of golf balls.

BRIEF DESCRIPTION OF THE DRAWINGS

These and further features of the present invention will be apparent with reference to the following description and drawings, wherein:

FIGS. 1A and 1B schematic views of a method and apparatus for inspecting the outer appearance of a golf ball according to one embodiment of the present invention, FIG. 1A being a perspective view and FIG. 1B being a side view.

FIG. 2 illustrates the relationship among a spherical article, illuminating light, and a line sensor camera used in the inspection method and apparatus of the invention.

FIGS. 3A-3D illustrate the principle of outer appearance inspection in the inspection method and apparatus of the invention.

FIGS. 4A-4H illustrate the principle of inspecting the outer appearance of a golf ball in the inspection method and apparatus of the invention.

DETAILED DESCRIPTION OF THE INVENTION

Figure 5:
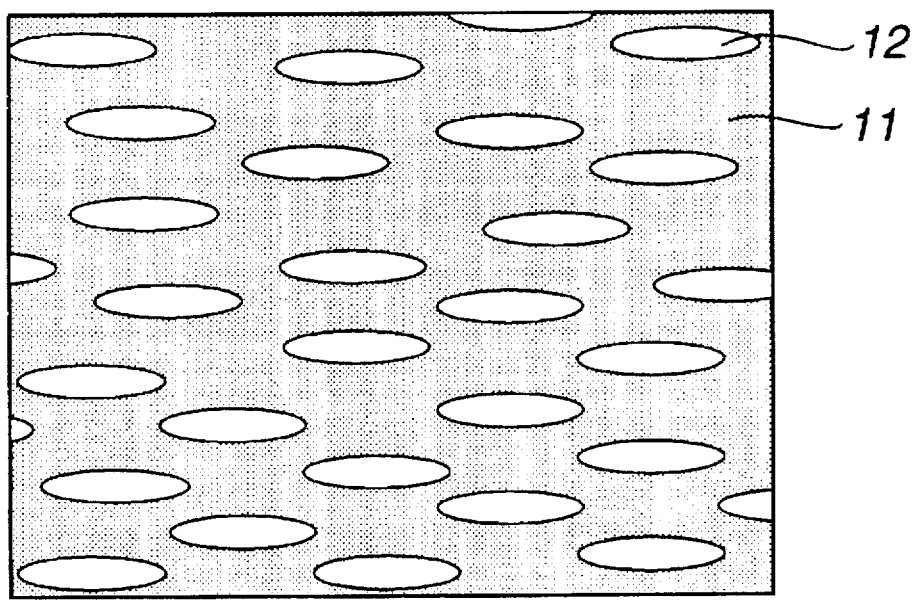
FIGS. 5A and 5B illustrate a two-dimensional image obtained in inspecting the outer appearance of a golf ball by the inspection method and apparatus of the invention, FIG. 5A being a two-dimensional image of a normal golf ball and FIG. 5B being a two-dimensional image of a bump-bearing golf ball.
Figure 5:
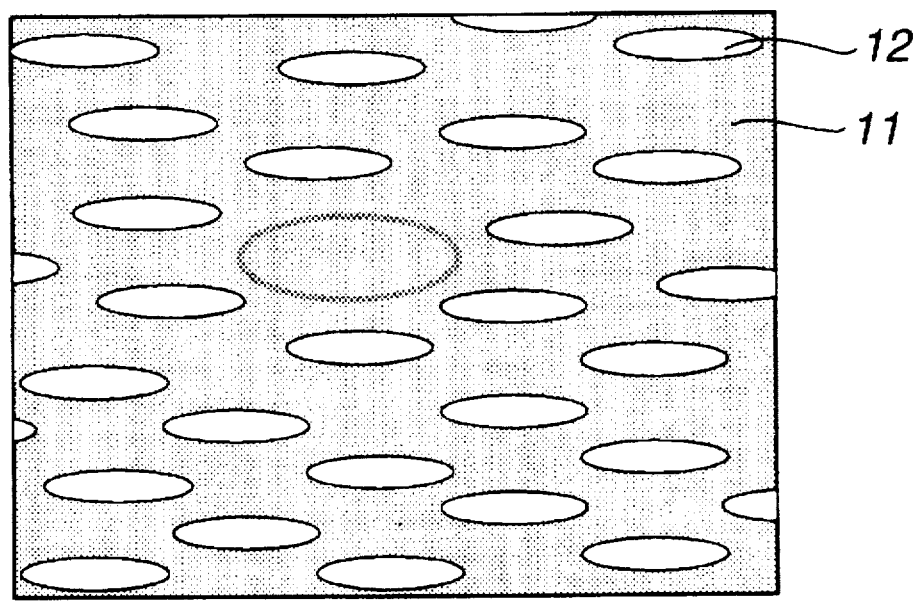

FIGS. 1 to 6 illustrate a method and apparatus for inspecting the outer appearance of a spherical article according to one embodiment of the invention.

According to the outer appearance inspecting method of the invention, a spherical article 1 to be inspected having a spherical surface is supported by rotating means in the form of a pair of rotatable support arms 2, 2. The spherical article 1 is supported in a stable attitude and rotated about an axis of the arms in one direction. From illuminating means in the form of a slit light projector 4, light 5 is illuminated to a selected position 3 on the spherical surface of the spherical article 1 in a tangential direction. A line sensor camera 6 is located above the axis of the arms 2 and oriented perpendicular to the light illuminating direction for taking a line image of the spherical surface in the vicinity of the selected position. The line sensor camera 6 delivers image data of the picture to an image processing means in the form of a computer (not shown) where a two-dimensional image is constructed from the image data. Any undesirable protrusion on the spherical surface is detected from the two-dimensional image.

More particularly, as best shown in FIG. 2, the rotational direction of the spherical article 1 coincident with the light illuminating direction shown by an arrow a. That is, the spherical article 1 is rotated such that a fixed point on its spherical surface may move along the light illuminating direction a as shown by an arrow b or c. With respect to the light illuminating direction a, the rotational direction may be either forward as shown by arrow b (counterclockwise as viewed in FIG. 1B) or backward as shown by arrow c. Most often and preferably, the spherical article 1 is rotated in a forward direction h with respect to the light illuminating direction a. The selected position 3 on the spherical surface is not a fixed position on the spherical surface, but a position determined from the correlation among the illuminating means 4, line sensor camera 6 and the spherical surface. The selected position moves along the spherical surface as the spherical article 1 rotates. The illuminating means 4 is not critical insofar as it can project light to produce highlight and shadow. A fiber light guide with a slit outlet is advantageously used since definite highlight and shadow areas are produced.

The line sensor camera 6 is designed for linearly imaging an object. In the present invention, the line sensor camera 6 takes a line picture of the spherical surface in the vicinity of the selected position 3 and along a straight line 7 perpendicular to the light illuminating direction a (the line 7 is in alignment with the rotation axis in the illustrated embodiment). The position at which the line sensor camera 6 takes a picture may be coincident with the point of contact between the light 5 and the spherical surface at the selected position 3 or shifted forward (away from the illuminating output 4) or backward (toward the illuminating output 4 as viewed in FIG. 1B) from the contact point. Where the spherical article 1 to be inspected is a golf ball having a plurality of dimples in the surface, it is preferred to take a picture at a position shifted forward (away from the illuminating output 4) from the contact point. This will be described later. The line sensor camera 6 is preferably oriented such that the angle θ between the axis of the camera 6 and the illuminating direction of light 5 is about 45 to 90 degrees, especially about 90 degrees as best shown in FIG. 1B. Even when the spherical surface is lustrous, this eliminates the inconvenience that light reflected by the spherical surface enters directly the line sensor camera 6 to produce a picture consisting of obscure bright and dark areas, ensuring that an abnormal brightness change due to the presence of an undesirable protrusion appears in the picture.

When the surface of the spherical article 1 is photographed in this way, the situation differs depending on the shooting position of the line sensor camera 6 as shown in FIG. 3A. When the shooting position of the line sensor camera 6 is at a position e shifted forward (away from the illuminating output 4) from the contact point 8 between the light 5 and the spherical surface, the shooting position e is always in the shadow shown by crosshatching lines in FIG. 3A. When the shooting position of the line sensor camera 6 is at a position f coincident with the contact point 8 or a position g shifted backward (toward the illuminating output 4) from the contact point 8, the shooting position f or g is always illuminated by the light 5. Then the resulting two-dimensional image is an overall uniformly dark image when the camera is at the shooting position e and an overall uniformly bright image when the camera is at the shooting positions f and g.

If an undesirable protrusion is present on the surface of the spherical article, an abnormal brightness change occurs in the two-dimensional image as shown in FIGS. 3B, 3C, and 3D. With regard to the shooting positions f and g, when an undesirable protrusion 9 comes in front of the shooting positions f and g with the rotation of the spherical article 1 as shown in FIGS. 3B and 3C, the undesirable protrusion 9 shuts out the light 5 so that the shooting positions f and g are in the shadow. As a result, a dark zone corresponding to this shadow appears in the two-dimensional image which should normally be an overall bright image. With regard to the shooting position 2, when the undesirable protrusion 9 comes to the shooting position e as shown in FIG. 3D, the undesirable protrusion 9 which is raised above the spherical surface is illuminated by the light 5. As a result, a bright zone corresponding to the illuminated protrusion appears in the two-dimensional image which should normally be an overall dark image.

In this way, any undesirable protrusion 9 on the surface of the spherical article 1 appears in the two-dimensional image as an abnormal brightness change whereby the undesirable protrusion 9 can be detected.

Next, where the article to be inspected is a golf ball 1a having a plurality of dimples in the surface, pictures are similarly taken on the ball as the ball rotates. The resulting situations are shown in FIGS. 4A to 4H. With regard to the shooting position e, when one side (left) edge of a dimple 10 comes to the shooting position e with the rotation of the golf ball 1a, the shooting position e is illuminated with the light 5 as shown in FIG. 4D. The shooting position e is kept illuminated with the light 5 until the light is shut out again by the opposite side (right) edge of the dimple 10 as shown in FIG. 4E. That is, the shooting position e is kept illuminated with the light 5 during rotation of the golf ball 1a from the state of FIG. 4D to the state of FIG. 4E while the shooting position e is kept in the shadow in other states.

Then when a two-dimensional image is constructed from image data taken at the shooting position e, bright spots 12 corresponding to dimples 10 appear on a dark background 11 in a white-spotted dapple pattern as shown in FIG. 5A.

With regard to the shooting position f, a dark spot appears in the two-dimensional image in a duration from the state of FIG. 4D to the state of FIG. 4G when the shooting position f is in a shadow zone created in the dimple 10 while the shooting position f is kept illuminated in other states. With regard to the shooting position g, a dark spot appears in the two-dimensional image in a duration from the state of FIG. 4C to the state of FIG. 4F when the shooting position g is in a shadow zone created in the dimple 10 while the shooting position g is kept illuminated in other states. Then in the two-dimensional image obtained from image data taken at the shooting position f or g, dark spots corresponding to dimples 10 appear on a bright background in a black-spotted dapple pattern. This image is a reversal of the image shown in FIG. 5A.

If an undesirable protrusion is present on the surface of the golf ball 1a, the change of shadow appearing on the ball surface is affected by this undesirable protrusion, bringing an abnormal change of brightness in the two-dimensional image. One exemplary situation is shown in FIG. 4. An explanation is now made with regard to shooting position e. If an undesirable protrusion 9a is present on the land 13 of the ball surface (the land is the ball surface where no dimples are formed), for the duration from FIG. 4D to FIG. 4E when the portion of the dimple 10 which should be normally illuminated with light 5 is at the shooting position e, the light 5 is shut out by the undesirable protrusion 9a and that portion is kept in the shadow. As a result, the dimple 10 which should normally appear as a bright spot in the two-dimensional image disappears. That is, the bright spot which should normally appear occults from the two-dimensional image as shown in FIG. 5B (the lost bright zone is encompassed by a phantom ellipsoid in the figure). A comparison of the image of FIG. 5B with the normal image of FIG. 5A clearly reveals the disappearance of a bright spot which should normally appear. If the undesirable protrusion 9a is large in size, in the state of FIG. 4A wherein the undesirable protrusion 9a comes at the shooting position e, the shooting position e which should normally be in the shadow is illuminated with light and consequently, a bright spot appears in the two-dimensional image where it should normally be dark. Similarly if an undesirable protrusion 9b is present within the dimple 10, for the duration from FIG. 4D to FIG. 4E when the shooting position e should normally be illuminated with light 5, the light 5 is shut out by the undesirable protrusion 9b to create a shaded portion, and consequently, the bright zone which should normally appear disappears from the two-dimensional image, obtaining an image as shown in FIG. 5B.

With regard to shooting position f, if an undesirable protrusion 9a is present on the land 13, in a duration from FIG. 4C to FIG. 4D, a forward portion of the dimple which should normally be bright is in the shadow of the undesirable protrusion 9a. Also when the land 13 arrives at the shooting position f after the dimple 10 goes past as shown in FIG. 4H, the shooting position f which should normally be bright is still kept in the shadow of the undesirable protrusion 9a. Although only the backward portion of the dimple 10 should normally appear as a dark spot in the two-dimensional image in a duration from FIG. 4D to FIG. 4G, the shooting position f is kept in the dark from the forward edge of the dimple 10 to the land 13 after passage of the dimple 10 past the shooting position f in a duration from FIG. 4C to FIG. 4H, so that the dark spot corresponding to the dimple 10 is increased. If an undesirable protrusion 9b is present within the dimple 10, the forward portion of the dimple 10 which should normally be bright is kept in the shadow of the undesirable protrusion 9b in a duration from FIG. 4C to FIG. 4D so that the dark spot corresponding to the dimple 10 is increased like the undesirable protrusion 9a on the land 13. As in the case of the shooting position f, with regard to the shooting position g, a forward portion of the dimple 10 which should normally be bright from FIG. 4B to FIG. 4C is kept in the shadow of the undesirable protrusion 9a or 9b and the land 13 which should normally be bright from FIG. 4F to FIG. 4G after the dimple 10 has passed past the shooting position g is now kept in the shadow of the undesirable protrusion 9b, the dark spot indicative of the dimple 10 in the two-dimensional image becomes larger than the normal dark spot.

In this way, according to the outer appearance inspecting method of the invention, even if the spherical article 1 to be inspected is a golf ball 1a having a plurality of dimples 10 in the surface, undesirable protrusions 9a, 9b on the ball surface appear in the two-dimensional image as abnormal changes of bright or dark spots whereby the undesirable protrusions 9a and 9b can be detected.

The outer appearance inspecting method of the invention is to detect undesirable protrusions 9, 9a, 9b on the surface of a spherical article 1 by detecting abnormal changes of bright or dark spots appearing in the two-dimensional image which is produced as mentioned above. The detection of abnormal changes of bright or dark spots appearing in the two-dimensional image can be done by the operator observing the two-dimensional image. Alternatively, judgment can be automated by storing a normal brightness change in a judgment means such as a computer, and comparing an actually detected brightness change with the normal change. The data representative of the normal brightness change to be stored in the judgment means are data of a normal two-dimensional image or data indicative of the presence/absence, population, distribution, and total area of bright or dark spots. Then inspection can be readily carried out even when the article to be inspected is a golf ball, because the golf ball can be supported by the support arms 2, 2 without taking into account its attachment direction (offset of the surface of a golf ball to be inspected).

Figure 6:
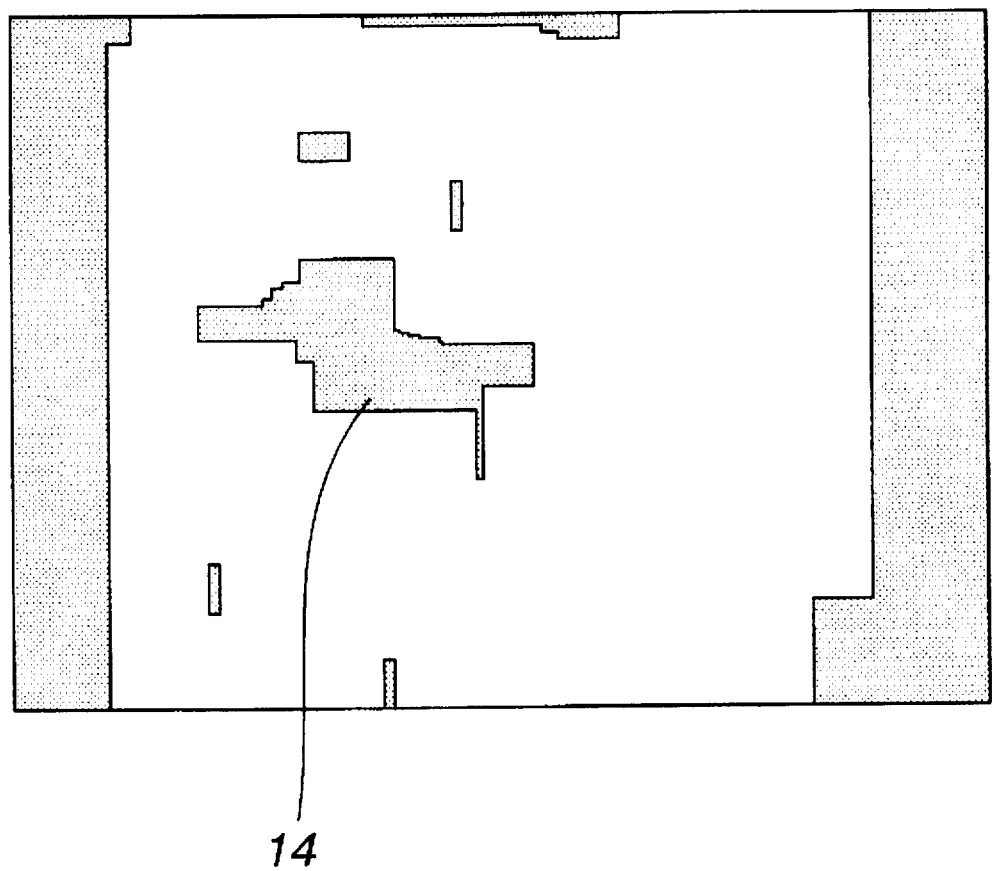
FIG. 6 illustrates an image obtained by processing the two-dimensional image of FIG. 5B so as to enlarge bright spots is expanded.

Upon detection of an abnormal brightness change from a two-dimensional image, the image may be processed to expand the bright or dark spots to exaggerate the abnormal brightness change, facilitating and ensuring the detection of undesirable protrusions. For example, when the two-dimensional image shown in FIG. 5B is processed to equally expand fully bright spots 12 indicative of dimples appearing in the image, as shown in FIG. 6, most dark zones are extinguished by the expanded bright spots and only the abnormal site which should normally be a bright spot, but becomes a dark zone (spot encompassed by an ellipsoid in FIG. 5B) due to the presence of an undesirable protrusion is left as a large dark zone 14. The abnormal change of bright and dark zones is exaggerated in this way. This ensures that the abnormal change of bright and dark zones due to the presence of an undesirable protrusions is readily detected. It is understood that such image processing can be readily carried out by image processing means such as a conventional computer. The same computer as used as an image converter for constructing a two-dimensional image and a judgment means for judging an abnormal change can also be used as the image processing means.

As mentioned above, in the outer appearance inspecting method of the invention, the shooting position of the line sensor camera 6 may be the position f coincident with contact point 8 between the light 5 and the spherical surface, the position e shifted forward (away from the illuminating output 4) from the contact point 8 or the position g shifted backward (toward the illuminating output 4) from the contact point 8. When a golf ball having a plurality of dimples in the surface is inspected for outer appearance, it is preferred to carry out inspection at the position e shifted forward (i.e. away from the illuminating output 4) from the contact point 8 between the light 5 and the spherical surface.

More particularly, with regard to the shooting position g shifted backward (toward the illuminating output 4) from the contact point 8 or the shooting position f coincident with contact point 8, an abnormal change of bright and dark zones appearing in the resulting two-dimensional image a mere enlargement of some of numerous dark zones distributed in the two-dimensional image in a dotted pattern as mentioned above. It is sometimes difficult to judge such enlargement and the exaggeration of the abnormality by image processing as mentioned above is less effective. With respect to the shooting position e shifted forward (away from the illuminating output 4) from the contact point 8, some of bright zones appearing in a dotted pattern totally disappear. Detection of an abnormal change of bright and dark zones is easier than in the case of the shooting positions f and g. When the abnormal change is exaggerated by image processing as mentioned above, the abnormal change becomes quite definite. With respect to the shooting position f coincident with the contact point 8, even a very small distortion on the spherical surface which gives rise to no problem in a substantial sense can bring out an abnormal change of bright and dark zones, prohibiting effective detection of only undesirable protrusions.

In this preferred embodiment, the shift w of the shooting position e from the contact point 8 (depicted in FIGS. 3A and 4A) is suitably determined in accordance with the size of undesirable protrusions 9, 9a, 9b to be inspected and the curvature of the spherical surface (size of the spherical article 1). If the shift w is small, the height difference h from the contact point 8 between light 5 and the spherical surface to the shooting position e is small, so that even a small distortion or convex on the spherical surface which gives rise to no problem in a substantial sense can be illuminated and detected as an abnormal change of bright and dark zones. If the shift w is large, on the other hand, the height difference h is large, so that only large undesirable protrusions can be detected. With this taken into account, the shift w is suitably determined in accordance with the accuracy of inspection and the type of the spherical article 1. For inspection of golf balls, the shift w is preferably set in the range of 0.1 mm to 10 mm, which results in a height difference h of up to 2.5 mm.

It is understood that the golf ball which is judged to have an undesirable protrusion by the inspection method of the invention is automatically picked up by a selector device cooperating with the judgment means such as the computer. Then the process from outer appearance inspection to removal of defective balls can be fully automated.

The outer appearance inspecting method and apparatus of the invention utilizes the fact that an article to be inspected is a spherical body such that when light 5 is illuminated to the selected position 3 on the spherical surface in a tangential direction, an abnormal change of bright and dark zones occurs at the selected position 3 as a result of an undesirable protrusion 9, 9a, 9b on the spherical surface 1, 1a shutting out the light 5 or being illuminated with the light 5. This abnormal change is detected by the line sensor camera 6 taking a picture along the straight line 7 extending at the selected position 3 perpendicular to the illuminating direction of light 5. The invention makes it possible to detect an undesirable protrusion in the form of a small bump on the spherical surface which is difficult to detect by the prior art technique. Since the illuminating direction of light 5 is a tangential direction at the shooting position, the shooting direction of the line sensor camera 6 can be offset 45 to 90 degrees from the illuminating direction of light 5. Even when the spherical surface is lustrous, this angular camera orientation eliminates the inconvenience that light reflected by the spherical surface enters directly the line sensor camera 6 to produce a picture consisting of obscure bright and dark zones, ensuring that an abnormal brightness change due to the presence of undesirable protrusions appears in the picture.

Even if the spherical article 1 to be inspected is a golf ball 1a having a plurality of dimples 10 in the surface, the outer appearance inspecting method of the invention can discriminate undesirable protrusions 9a, 9b from the normal spherical surface, ensuring automatic high precision outer appearance inspection. When outer appearance inspection is carried out on a golf ball 1a having a plurality of dimples 10 in the surface according to the present invention, there is obtained a two-dimensional image in which a plurality of bright or dark spots corresponding to the plurality of dimples 10 appear in a dotted pattern. If undesirable protrusions 9a, 9b are present on the surface of golf ball 1a, the protrusions 9a, 9b shuts out the illuminating light or are illuminated with the illuminating light independent of whether the protrusions 9a, 9b are inside or outside the dimples 10, necessarily resulting in a two-dimensional image having an abnormal change of bright and dark zones, whereby the presence of undesirable protrusions can be acknowledged. Undesirable protrusions can be automatically detected from the two-dimensional image if a judgment means such as a computer is used.

The outer appearance inspecting method and apparatus according to the invention is not limited to the above-mentioned embodiments and many modifications may be made thereto. The rotating means for supporting and rotating the spherical article 1, 1a and the illuminating means are not limited to the illustrated ones. The two-dimensional image may be processed in a manner other than the above-mentioned one such that an abnormal change of bright and dark zones may be detected. With respect to the remaining components, various modifications may be made without departing from the scope and spirit of the invention.

The method and apparatus for inspecting the outer appearance of a spherical article according to the invention makes it possible to detect an undesirable protrusion in the form of a small bump on the spherical surface and to automate the detection process. Since even small undesirable protrusions on the spherical surface having a plurality of recesses or dimples can be detected, the inventive method and apparatus can be advantageously used in inspecting the outer appearance of golf balls.

We claim:

1. A method for inspecting the outer appearance of a spherical article, comprising the steps of:

illuminating light to a selected position on the spherical surface of the spherical article in a tangential direction, rotating the spherical article in line with the light illuminating direction, operating a line sensor camera to take a line image of the spherical surface in the vicinity of the selected position and along a line perpendicular to the light illuminating direction, the line sensor camera delivering image data, constructing a two-dimensional image from the image data, and detecting an abnormal brightness change which appears in the two-dimensional image as a result of an undesirable protrusion on the spherical surface shutting out the light, thereby detecting the presence of the undesirable protrusion.

2. The outer appearance inspecting method of claim 1 wherein the shooting position at which the line sensor camera takes a picture is slightly shifted from the point of contact between light and the spherical surface at the selected position away from a means for illuminating light.

3. The outer appearance inspecting method of claim 1 wherein the spherical article is a golf ball.

4. The outer appearance inspecting method of claim 1 further comprising the step of processing the two-dimensional image so as to enlarge bright or dark spots therein for exaggerating the abnormal brightness change appearing in the two-dimensional image.

5. An apparatus for inspecting the outer appearance of a spherical article, comprising rotating means for supporting and rotating the spherical article in a predetermined direction at a predetermined speed, means for illuminating light to a selected position on the spherical surface of the spherical article in a tangential direction and in line with the rotational direction of the spherical article, a line sensor camera for taking a line image of the spherical surface in the vicinity of the selected position and along a line perpendicular to the light illuminating direction, and image converter means for receiving image data from the line sensor camera and constructing a two-dimensional image from the image data, wherein an abnormal brightness change which appears in the two-dimensional image as a result of an undesirable protrusion on the spherical surface shutting out the light is detected, thereby detecting the presence of the undesirable protrusion.

6. The outer appearance inspecting apparatus of claim 5 wherein the shooting position at which the line sensor camera takes a picture is slightly shifted from the point of contact between light and the spherical surface at the selected position away from the illuminating means.

7. The outer appearance inspecting apparatus of claim 5 further comprising means for processing the two-dimensional image so as to enlarge bright or dark spots therein for exaggerating the abnormal brightness change appearing in the two-dimensional image.

8. A method for inspecting the outer appearance of a spherical article, comprising the steps of:

illuminating light to a selected position on the spherical surface of the spherical article in a tangential direction, rotating the spherical article in line with the light illuminating direction, operating a line sensor camera to take a line image of the spherical surface in the vicinity of the selected position and along a shooting direction in an angular range of 45 to 90 degrees to the light illuminating direction, the line sensor camera delivering image data, constructing a two-dimensional image from the image data, and detecting an abnormal brightness change which appears in the two-dimensional image as a result of an undesirable protrusion on the spherical surface shutting out the light, thereby detecting the presence of the undesirable protrusion.

9. The outer appearance inspecting method of claim 8 wherein the shooting position at which the line sensor camera a picture is slightly shifted from the point of contact between light and the spherical surface at the selected position away from a means for illuminating light.

10. The outer appearance inspecting method of claim 8 wherein the spherical article is a golf ball.

11. The outer appearance inspecting method of claim 8 further comprising the step of processing the two-dimensional image so as to enlarge bright of dark spots therein for exaggerating the abnormal brightness change appearing in the two-dimensional image.

12. An apparatus for inspecting the outer appearance of a spherical article, comprising rotating means for supporting and rotating the spherical article in a predetermined direction at a predetermined speed, means for illuminating light to a selected position on the spherical surface of the spherical article in a tangential direction and in line with the rotational direction of the spherical article, a line sensor camera for taking a line image of the spherical surface in the vicinity of the selected position and along a line forming an angle of 45 to 90 degrees to the light illuminating direction and, image converter means for receiving image data from the line sensor camera and constructing a two-dimensional image from the image data, wherein an abnormal brightness change which appears in the two-dimensional image as a result of an undesirable protrusion on the spherical surface shutting out the light is detected, thereby detecting the presence of the undesirable protrusion.

13. The outer appearance inspecting apparatus of claim 12 wherein the shooting position at which the line sensor camera takes a picture is slightly shifted from the point of contact between light and the spherical surface at the selected position away from the illuminating means.

14. The outer appearance inspecting apparatus of claim 12 comprising means for processing the two-dimensional image so as to enlarge bright or dark spots therein for exaggerating the abnormal brightness change appearing in the two-dimensional image.

* * * * *